United States Patent
Ibsies

(10) Patent No.: US 10,251,735 B2
(45) Date of Patent: Apr. 9, 2019

(54) SPECIALIZED KEYBOARD FOR DENTAL EXAMINATIONS

(76) Inventor: Fadi Ibsies, Tigard, OR (US)

( * ) Notice: Subject to any disclaimer, the term of this patent is extended or adjusted under 35 U.S.C. 154(b) by 793 days.

(21) Appl. No.: 13/441,637

(22) Filed: Apr. 6, 2012

(65) Prior Publication Data

US 2012/0194546 A1   Aug. 2, 2012

Related U.S. Application Data

(63) Continuation-in-part of application No. 12/544,074, filed on Aug. 19, 2009, now abandoned.

(51) Int. Cl.
| | | |
|---|---|---|
| *A61C 19/00* | (2006.01) | |
| *G16H 40/63* | (2018.01) | |
| *G06F 3/02* | (2006.01) | |
| *G06F 19/00* | (2018.01) | |

(52) U.S. Cl.
CPC ............ *A61C 19/00* (2013.01); *G06F 3/0219* (2013.01); *G06F 19/00* (2013.01); *G16H 40/63* (2018.01)

(58) Field of Classification Search
None
See application file for complete search history.

(56) References Cited

U.S. PATENT DOCUMENTS

| | | | | |
|---|---|---|---|---|
| D262,204 S | * | 12/1981 | Wilson | D14/335 |
| D270,272 S | | 8/1983 | Steele | |
| 4,906,117 A | * | 3/1990 | Birdwell | B41J 5/10 400/472 |
| 4,915,626 A | | 4/1990 | Lemmey | |
| 4,963,044 A | | 10/1990 | Warner | |
| 4,974,183 A | | 11/1990 | Miller | |
| 5,033,238 A | | 7/1991 | Zubler | |
| 5,084,833 A | | 1/1992 | Matsuda et al. | |
| 5,235,510 A | | 8/1993 | Yamada et al. | |
| 5,303,148 A | | 4/1994 | Mattson et al. | |
| 5,562,448 A | | 10/1996 | Mushabac | |
| 5,584,588 A | | 12/1996 | Harbaugh | |
| 5,600,313 A | | 2/1997 | Freedman | |

(Continued)

FOREIGN PATENT DOCUMENTS

| | | |
|---|---|---|
| EP | 1559390 | 1/2005 |
| EP | 1559390 | 8/2005 |

(Continued)

OTHER PUBLICATIONS

Clark Dental Support, "Florida Probe Support," at least as early as Jun. 29, 2015, web site, http://www.clarkdentalsupportco.uk/florida_probe_support.php, 2 pages.

(Continued)

*Primary Examiner* — Stella Higgs
(74) *Attorney, Agent, or Firm* — Law Office of Karen Dana Oster, LLC

(57) ABSTRACT

The present invention includes a device, system and method of use consisting of a specialized dental keyboard wherein the specialized keyboard resides as virtual keys on a touch screen panel on a device such as a tablet computer including such devices as an Apple iPad. The invention includes a software component that enables customer configurable keyboard layouts including a plurality of specialized keys that provide short-cut macros to streamline data entry during a dental exam.

19 Claims, 10 Drawing Sheets

(56) References Cited

U.S. PATENT DOCUMENTS

| | | |
|---|---|---|
| 5,742,700 A | 4/1998 | Yoon et al. |
| 5,752,827 A | 5/1998 | Baron et al. |
| 5,944,531 A | 8/1999 | Foley et al. |
| 6,010,260 A | 1/2000 | Chao |
| 6,227,850 B1 | 5/2001 | Chishti et al. |
| 6,241,406 B1 | 6/2001 | Yan |
| 6,295,052 B1* | 9/2001 | Kato ............... G06F 3/04886 341/21 |
| 6,501,462 B1 | 12/2002 | Garner |
| 6,664,986 B1 | 12/2003 | Kopelman et al. |
| 7,010,153 B2 | 3/2006 | Zimmermann |
| D523,433 S * | 6/2006 | O'Neil ............... G06F 3/0231 D14/396 |
| D533,875 S | 12/2006 | Miles et al. |
| D552,118 S | 10/2007 | Jung et al. |
| D565,046 S | 3/2008 | Ward |
| 7,343,305 B2 | 3/2008 | Benn et al. |
| D567,249 S | 4/2008 | Gunn et al. |
| 7,354,402 B2 | 4/2008 | Hoarau et al. |
| 7,369,116 B2 | 5/2008 | Logue |
| D573,989 S | 7/2008 | Ward |
| 7,454,705 B2 | 11/2008 | Cadez et al. |
| 7,478,327 B1* | 1/2009 | Reid ............... G06F 3/005 715/719 |
| D590,836 S | 4/2009 | Schneider |
| D602,495 S | 10/2009 | Um et al. |
| D607,890 S | 1/2010 | Beavers et al. |
| D611,054 S | 3/2010 | Lin et al. |
| 7,689,317 B2 | 3/2010 | McGrady et al. |
| D614,644 S | 4/2010 | Kristensson et al. |
| D614,645 S | 4/2010 | Kristensson et al. |
| D617,336 S | 6/2010 | Beavers et al. |
| D617,337 S | 6/2010 | Beavers et al. |
| D619,608 S | 7/2010 | Meziere |
| D619,611 S | 7/2010 | Meziere |
| D621,410 S | 8/2010 | Verfuerth et al. |
| 7,819,598 B2 | 10/2010 | Griffin |
| D629,414 S | 12/2010 | Beavers et al. |
| D629,415 S | 12/2010 | Beavers et al. |
| D633,097 S | 2/2011 | Jewitt et al. |
| D638,852 S | 5/2011 | Skidmore et al. |
| D663,742 S | 7/2012 | Tanghe et al. |
| D664,549 S | 7/2012 | Gleasman et al. |
| D664,962 S | 8/2012 | Duggan et al. |
| D664,963 S | 8/2012 | Duggan et al. |
| D664,964 S | 8/2012 | Odell et al. |
| D665,394 S | 8/2012 | Duggan et al. |
| D675,218 S | 1/2013 | Arnold et al. |
| D679,722 S | 4/2013 | Ray |
| D682,293 S | 5/2013 | Kanalakis, Jr. et al. |
| D684,172 S | 6/2013 | Rytt et al. |
| D684,173 S | 6/2013 | Rytt et al. |
| D684,177 S | 6/2013 | Winther et al. |
| D684,588 S | 6/2013 | Gilani |
| D690,318 S | 9/2013 | Kluttz et al. |
| D690,723 S | 10/2013 | Steele et al. |
| 8,624,842 B2 | 1/2014 | Rouchouze |
| D705,799 S | 5/2014 | Funabashi et al. |
| D708,638 S | 7/2014 | Manzari et al. |
| D709,910 S | 7/2014 | Pasquero et al. |
| D711,897 S | 8/2014 | Chaudhri |
| D712,420 S | 9/2014 | Song et al. |
| D712,913 S | 9/2014 | Na |
| D717,825 S | 11/2014 | Pasquero et al. |
| 8,931,969 B2 | 1/2015 | Stewart et al. |
| D737,328 S | 8/2015 | Watson et al. |
| D738,903 S | 9/2015 | Lee |
| D739,861 S | 9/2015 | Perez et al. |
| D742,872 S | 11/2015 | Akana et al. |
| 9,195,818 B2 | 11/2015 | Ferren |
| D746,833 S | 1/2016 | Kim et al. |
| 9,235,271 B2 | 1/2016 | Berg |
| D749,085 S | 2/2016 | Furue et al. |
| D750,649 S | 3/2016 | Jung et al. |
| D754,719 S | 4/2016 | Zha |
| D755,809 S | 5/2016 | Kim et al. |
| D757,098 S | 5/2016 | Ekholm et al. |
| D758,411 S | 6/2016 | Lee |
| D758,417 S | 6/2016 | Chaudhri et al. |
| D758,427 S | 6/2016 | Park et al. |
| D759,095 S | 6/2016 | Seo et al. |
| D759,096 S | 6/2016 | Seo et al. |
| D763,890 S | 8/2016 | Pan |
| D765,671 S | 9/2016 | Katopis |
| D765,708 S | 9/2016 | Gagnier |
| D765,721 S | 9/2016 | Senders |
| D767,609 S | 9/2016 | Mehrzad |
| D769,934 S | 10/2016 | Chaudhri et al. |
| D771,089 S | 11/2016 | Guntzer et al. |
| D774,525 S | 12/2016 | Seo et al. |
| D775,171 S | 12/2016 | Gottlieb |
| D775,649 S | 1/2017 | Anzures et al. |
| D775,655 S | 1/2017 | Ibsies |
| D776,133 S | 1/2017 | Hill et al. |
| D777,202 S | 1/2017 | Maeda et al. |
| D778,927 S | 2/2017 | Bertnick et al. |
| D779,536 S | 2/2017 | Wingate-Whyte et al. |
| D779,558 S | 2/2017 | Ibsies |
| D780,198 S | 2/2017 | Cao |
| D780,200 S | 2/2017 | Chaudhri |
| D780,800 S | 3/2017 | Bi |
| D781,339 S | 3/2017 | Li et al. |
| D781,872 S | 3/2017 | Wu et al. |
| D786,927 S | 5/2017 | Ibsies |
| D787,555 S | 5/2017 | Ibsies |
| D788,153 S | 5/2017 | Kim et al. |
| D789,378 S | 6/2017 | Gottlieb |
| D790,569 S | 6/2017 | Anzures et al. |
| D797,766 S | 9/2017 | Ibsies |
| D798,894 S | 10/2017 | Ibsies |
| 2002/0178032 A1* | 11/2002 | Benn et al. ............... 705/2 |
| 2004/0015327 A1* | 1/2004 | Sachdeva et al. ............ 702/167 |
| 2004/0036632 A1* | 2/2004 | Ford ............... G06F 3/0238 341/22 |
| 2004/0095507 A1 | 5/2004 | Bishop |
| 2004/0158507 A1 | 8/2004 | Meek, Jr. et al. |
| 2004/0236608 A1 | 11/2004 | Ruggio et al. |
| 2005/0043970 A1 | 2/2005 | Hsieh |
| 2005/0286953 A1* | 12/2005 | Griffin ............... G06F 1/1626 400/486 |
| 2007/0128574 A1 | 6/2007 | Kuo et al. |
| 2007/0239488 A1* | 10/2007 | DeRosso ............... G06F 19/321 705/3 |
| 2007/0244581 A1 | 10/2007 | Nyholm |
| 2008/0018598 A1 | 1/2008 | Marsden |
| 2009/0027334 A1* | 1/2009 | Foulk ............... G06F 3/04886 345/157 |
| 2009/0183098 A1 | 7/2009 | Casparian et al. |
| 2010/0121658 A1 | 5/2010 | Kaminski et al. |
| 2011/0043451 A1 | 2/2011 | Ibsies |
| 2012/0032945 A1 | 2/2012 | Dare et al. |
| 2012/0120181 A1 | 5/2012 | Kanalakis, Jr. |
| 2012/0194546 A1 | 8/2012 | Ibsies |
| 2012/0274661 A1 | 11/2012 | Ye et al. |
| 2014/0002364 A1 | 1/2014 | Ibsies |
| 2014/0337049 A1 | 11/2014 | DeBusk et al. |
| 2015/0135108 A1 | 5/2015 | Pope et al. |

FOREIGN PATENT DOCUMENTS

| | | |
|---|---|---|
| WO | WO02091279 | 11/2002 |
| WO | WO2002091279 | 11/2002 |
| WO | WO2014086691 | 6/2014 |

OTHER PUBLICATIONS

Datacon Dental Systems, "Charting Overview," at least as early as May 4, 2015, web site, http://www.datacondental.com/charting-overview, 1 page.

Dental Equipment Center, "Dental Equipment Store—Kavo Dental Equipment," at least as early as Jun. 29, 2015, web site, http://www.dentalequipmentcenter.com/kavo-dental.html, 3 pages.

(56) References Cited

OTHER PUBLICATIONS

DentiMax, "DentiMax Software," as early as May 4, 2015, web site, http://www.softwareadvice.com, 1 page.
Health and Medicine, Spinoff 2008, "Periodontal Probe Improves Exams, Alleviates Pain," Originating Technology/NASA Contribution, at least as early as 2008,. 2 pages.
Perio-Imaging, "Periodontal Gum Disease," at least as early as Jun. 29, 2015, web site, http://www.perioimaging.com/pages/products.aspx, © 2008 Perio-Imaging Inc., all rights reserved, 11 pages.
ProbeOne, "The Gentle Probe," at least as early as Jun. 29, 2015, © 1995-2011 Probe One, web site, http://www.probeone.com/standardized.htm, 2 pages.
Technology Transfer Program, Bringing NASA Technology Down to Earth, "Periodontal Probe Improves Exams, Alleviates Pain," at least as early as Jun. 29, 2015, web site, https://spinoff.nasa.gov/Spinoff2008/hm_8.html, 2 pages.
Unident Software Company, "Axex Dental Software," web site, at least as early as May 4, 2015, http://www.softwareadvice.com, 1 page.
Krantz, Peter, "The Ideal VIM Keyboard," at least as early as Nov. 11, 2016, http://wwwpeterkranz.com/2006/vim-keyboard/, 7 pages.
DenChart Periodontal Software, "DenChart comes packed with features and power tools," http://www.denchart.com/features, Internet Archive WayBackMachine, at least as early as Dec. 15, 2009, 2 pages.
United States Patent and Trademark Office, "U.S. Appl. No. 61/113,822," Provisional of 2010/0121658, Kaminski, et al., filed Nov. 12, 2008, 29 pages.

\* cited by examiner

SPECIALIZED KEYBOARD FOR DENTAL EXAMINATIONS

PRIORITY CLAIM

This application is a continuation in part of earlier filed, non-provisional and co-pending U.S. patent application Ser. No. 12/544,074, which was filed on 19 Aug. 2009 by the same inventor. The present application is based on and claims priority from this application pursuant to 35 USC 120 and that disclosure is hereby expressly incorporated herein by reference.

BACKGROUND

This invention relates to specialized input devices, specifically a keyboard and method of use and software related to periodontal examinations.

A periodontal examination, an important procedure performed frequently in dental and periodontal offices, includes an examination of the bones holding the teeth in place and the conditions of the teeth and gums. The examination includes probing the teeth and the gums around each of the patient's teeth in succession, and recording the results. Because the examination requires several measurements for each of the (normally) 32-teeth, a large amount of data is generated and must be recorded.

The data output from the examination of a patient is recorded on a chart. Today, the dental chart —no longer a paper record hand-written by the dentist—is a computerized system including a user interface, input device and database. Accordingly, today's dentist electronically inputs a patient's dental examination into a computerized record associated with the patient. This record requires the dentist or his assistant to input the patient's examination. Preferably, this input occurs real-time to avoid errors and reduce inefficient duplication of effort.

However, real-time data entry while also maintaining a safe and clean environment free of risk of contamination of infectious disease requires a time intensive operation requiring two persons (examiner and data-entry person). In some instances specialized tools are used to facilitate the exam and real-time data recording, but most often a standard keyboard and/or touch screen and/or mouse or other point-and-click input device is used by the assistant while the dentist probes and examines each tooth and audibly notes the condition. In turn the assistant keys in the audible notes via a standard keyboard or touch screen into the electronic chart for the dental patient.

This dental chart often includes notations and records of the locations of carious, broken and missing teeth along with work previously performed by another dentist, including restorations, crowns and bridges. To improve efficiencies, various prior art methods and devices have been introduced to record and retain patient records on a varied form of the dental chart.

One such improvement includes U.S. Pat. No. 7,343,305 granted to Benn et al. on 11 Mar. 2008. Benn teaches a method and system for charting tooth decay and discloses a conventional input device and computer for entering tooth condition during an examination. Particularly, it discloses a method and system for advanced caries management that provides more descriptive representations of tooth decay, including site severity, activity (demineralization or remineralization), and cavitation state (non-cavitated or cavitated) of decay. Benn teaches a need in the art for a simple graphical user interface (GUI) to make entering and viewing data relative to caries management easier. A conventional GUI display includes a desktop metaphor upon which one or more icons, application windows, or other graphical objects are displayed. Typically, a user interacts with a GUI display utilizing a graphical pointer, which the user controls with a graphical pointing device, such as a mouse, touch pen, trackball, or joystick. The user selects icons or other graphical objects within the GUI display by positioning the graphical pointer over the graphical object and depressing a button associated with the graphical pointing device. In addition, the user can typically relocate icons, application windows, and other graphical objects on the desktop utilizing the well-known drag-and-drop techniques. By manipulating the graphical objects within the GUI display, the user can control the underlying hardware devices and software objects represented by the graphical objects in a graphical and intuitive manner.

Other known methods and devices, relating particularly to input devices, include U.S. Pat. No. 5,752,827 issued on 19 May 1998 to Baron et al., which teaches a specialized input keyboard specifically adapted for inputting tooth conditions during a dental examination. FIGS. 3, 4, 5, 6, and 7 of Baron et al. show a generally rectilinear, thin, portable, input keyboard with standard alpha-numeric keys arranged in a conventional row/column layout. Baron et al. further teaches a method of special codes representing combinations of a tooth and a condition.

U.S. Pat. No. 7,354,402 issued on 8 Apr. 2008 to Hoarau et al. teaches an intra-oral data input tool including a discoid head and handle. The discoid head includes a data input device responsive to force applied by a stylus and may be used directly by contacting a tooth during a dental examination.

Yet other methods and devices, relating particularly to output or display improvement include U.S. Pat. No. 5,944,531 issued on 31 Aug. 1999 to Foley et al., which teaches an instructional display of a human mouth; and U.S. Pat. No. 6,664,986 issued on 16 Dec. 2003 to Kopelman et al., which teaches a graphical user interface and display of a representation of a human mouth in simulated 3-D.

One improved input device for periodontal examinations includes the teaching of Baron et al. in U.S. Pat. No. 5,752,827 issued on 19 May 1998. Baron teaches an automated periodontal examination data recording and recall apparatus having at least one pre-programmed mode of operation. Periodontal examination data is entered in a predetermined sequence into the Baron apparatus. The periodontal examination must be performed in a predetermined sequence. The periodontal examination apparatus includes a keypad input device, an LCD, a main controller, and an attachment device for securing the apparatus to the examiner's arm.

Despite the attempts at improving the methods and devices to improve efficiency of data collection during a dental examination, there remains a need for an easy-to-use, customized or specialized keyboard that enables rapid data entry in any sequence tailored to the needs of a periodontal examination. Such a keyboard must adapt to existing computer hardware and software systems commonly used in dental offices.

SUMMARY OF THE INVENTION

The present invention, in various preferred embodiments, includes an input device for use with a computerized system and a method of use of the keyboard can be implemented in numerous ways, including as a component of a computer or database system, a method of data input, an apparatus, an apparatus connected to a computer readable medium, a computer program product, or a data structure tangibly fixed in a computer readable memory. Several embodiments of the invention are discussed below.

As a computer system, an embodiment of the invention includes a memory unit containing data, a display, and a processor unit. The system may be, for example, in the form of a desktop, laptop, handheld or palm-sized device, a personal data assistant (PDA), or integrated with other devices. The display has at least one display area (window). The processor unit operates to receive input from the user (keyboard, mouse, pen, voice, touch screen, or any other means by which a human can input data into a computer, including through other programs such as application programs or devices such as a probe), store the input as data, and output the data to the screen or printer. The data may also be transmitted to another device, such as a computer, or transferred via electronic means (including Internet communications). The memory unit may store the protocol for the method of recording carious lesions.

The display device may include icons representative of the method of the present invention. The computer system further includes a graphical user interface (GUI) for the display screen for searching, inputting, and displaying data. A variety of formats for searching, inputting, and displaying data is contemplated.

In one preferred embodiment, a graphical representation of all of the teeth of a patient is displayed on a device (such as a computer screen) from which a specific tooth is selected via the specialized keyboard of the present invention. That tooth is then displayed with individual anatomical graphical regions delineated. The region on the display that corresponds to the region on the actual tooth being examined is selected (or the regions can be automatically activated in a predetermined order). If using a digital probe, the reading on the probe is recorded (directly or manually) for the selected region on the screen. If manual probing is conducted, the operator enters the appropriate data for that region. Voice recognition and voice output may be used in conjunction with the method. Readings are recorded for each region as necessary. The process is repeated for each tooth as necessary. A printout of the chart can be provided from the device or from a central system with which the device communicates (e.g., PDA synchronized with desktop).

As a computer readable media containing program instructions, an embodiment of the invention includes: computer readable code devices for the specific operations of the invention, including graphical display of the teeth, unique display of regions for systematic examination, input of data (manually or directly from another instrument), recording of data, display of data, and output of data. The methods of the present invention may be implemented as a computer program product with a computer-readable medium having code thereon. The program product includes a program and a signal bearing media bearing the program.

As an apparatus, the present invention may include at least one specialized keyboard coupled to a processor, a memory coupled to the processor, and a program residing in the memory which implements the methods of the present invention.

One preferred embodiment of the present invention includes an apparatus comprising a specialized dental keyboard. This keyboard will revolutionize the way data is entered in all dental offices and schools, reduce errors due to misdiagnosis, and increase the accuracy of data entry of patient's existing conditions prior to rendering treatment. This data entry device seamlessly integrates with existing patient management software via key macros and direct software bridging. The keyboard includes keys (separate keys or combinations of keys) representing all teeth numbers, including primary teeth, based on the Universal/National System primarily used in the United States.

The Universal/National System for permanent (adult) dentition (1-32) starts at the patient's upper right molar (1) and follows around the upper arch to the upper left third molar (16), descending to the lower left third molar (17) and follows around the lower arch to the lower right third molar (32). The Universal/National System order for the primary (baby) dentition is the same as described for the permanent dentition, however, the primary teeth are designated by upper case letters A through T, with A being the patient's upper right second primary molar and T being the lower right second primary molar.

Accordingly, the present invention utilizes this Universal system and functions as an improved dental pathosis and treatment plan entry device. The present invention enables the operator (such as a dental assistant, dental hygienist or a dentist, for example) to enter data into pre-determined software linked via a software bridge and key macros making the entry of data more accurate and providing protection for both the dentist and the patient as far as the data entry is concerned. This data provides the existing conditions present in the patient's mouth and the treatment plan needed to correct these conditions. The patient will be able to have a complete diagnosis and have a better understanding of the conditions that exist in his mouth. This device enables connection to certain educational videos that the patient will be able to benefit from and get a better understanding of the need for the recommended treatment. This device improves the data-entry operation for a tooth and includes short cuts (keys and/or macros) for existing conditions, a link with intraoral images of the tooth, a link with the periodontal assessment of the tooth, and is able to select any combination of several different treatment options including placement of the correct fees for each procedure and American Dental Association (ADA) codes for each procedure.

The keyboard of the present invention, therefore, better enables a doctor or dentist to efficiently create a record of past work ("what was done" or "existing"), what needs to be done, why it needs to be done, and the long term prognosis of the procedure based on the periodontal health of the tooth —all the essential data a board of dentistry requires to protect both the patient and the doctor. This device can become the educational tool of the future if schools were to carry this device and make incoming dental students use it as the standard of care in data entry.

This keyboard works with existing dental software tools that are available on the market and it will be made compatible via software bridges or patches, or in future software that can be specifically developed for it. One example of existing software for which the present invention is well-suited includes the Dentrix brand software tool available from http://www.dentrix.com, which is a readily available dental software tool and is well-known in this art. Other examples of compatible software include the Eaglesoft brand (available from http://patterson.eaglesoft.net/index.htm), Daisy Dental Software (available from http://www.daisydental.com/software/index.shtml), and Kodak-brand dental software (available from http://www.kodakdental.com/for-dentists/practice-management-systems/softd-ent.aspx).

The present invention comprises a keyboard with dental specific buttons, each button representing a tooth on the first two rows of keys including a shift-like key on the right side that toggles between primary and permanent teeth. On the left side is the dental diagnosis and treatment section. The following symbols and abbreviations are used: EX=existing condition, whether it is a filling (type of filling), broken half of tooth, decay on a certain spot on the tooth; DX=what is wrong with the tooth, and why it needs treatment, such as a failing alloy filling, open margins, or recurrent decay on mesial; and TX=recommended treatment, for example, what is the proposed treatment, a crown, gold inlay, porcelain inlay or just a composite filling. There will be a toggle to choose different options of treatment, such as root canal #30, removal #30, or an implant.

Press the probing chart and the computer will automatically pull up the patient's periodontal chart.

On the right side of the device is the periodontal health of the tooth. It is represented with the most common buttons for millimeter readings of the periodontal pockets from 1-6 mm. The less common millimeter measurements are represented with smaller buttons 7-12 mm for each tooth. A bleeding point button can be pressed for the mesial, middle reading, and distal reading for example tooth #2 has a facial reading of 3-5-4 with bleeding points on both mesial and middle reading. The sequence of buttons that will be pressed #2 on the upper left then b1, b2, on the probing chart 3-5-4 and then mobility class I. This will give a very accurate reading of the existing periodontal condition of tooth #2.

Pressing the image capture button causes the computer to pull up the intra-oral camera.

One contemplated method includes using the keyboard to assist with dental photographs (pictures). Accordingly, the way pictures will be taken is that the assistant, for example, will press the #4 key and the camera will become active and will point to #4, and the image will be stored in the patient's computer chart as tooth #4. Thus, when data is pulled for tooth #4 there will be an existing condition of what the patient's tooth looked like when they first joined the practice, along with an image of the tooth, the periodontal health of the tooth, what the proposed treatment was at the time, and the treatment that was rendered on the tooth.

An assistant, doctor or hygienist can enter a full treatment plan on this keyboard without having to use a mouse because using a mouse in the dental operatory is awkward at best and tends to really slow down the data entry which causes the assistant to skip over pertinent data.

The LCD display displays the data entered and has a 2 sec. time lapse so that data can be reviewed prior to having it sent to the software. This way, the person entering the data can intercept it and change it if he/she sees that they made a mistake in the data entry.

One embodiment of the present invention contemplates a specialized dental keyboard/input-output device adapted for use with a host computer to record conditions of teeth in a patient during a dental exam using a dental examination software tool resident on the host computer. The device comprises: a wired or wireless connection coupled to the host computer for sending inputted data representing a plurality of keystrokes; a set of programming sequences resident on the host computer adapted to convert the inputted keystrokes to a data string recognizable by the dental examination software tool; a plurality of input keys arranged on a keyboard, each key communicating to the wired or wireless connection; and a liquid-crystal display screen mounted on the keyboard and adapted to display a sequence of keystrokes.

This embodiment further contemplates that the plurality of input keys consists of at least 32 keys wherein each key is consecutively numbered beginning with digit "1" and ending with the combination digits "32" indicating each one of the thirty-two teeth.

This embodiment further contemplates a first-condition key on the keyboard and a second condition key wherein the first condition key represents the patient's current condition and a second condition key represents the patients proscribed treatment.

This embodiment further contemplates a second multidirectional input element having at least five unique input directions, the five input directions disposed generally in a common input plane; and wherein the plurality of input keys comprises a first set of keys numbered from 1 to 32, the first set of keys being adapted to input the current condition of the patient's teeth; and a second set of keys numbered from 1 to 32, the second set of keys being adapted to input the treatment or proscribed treatment of the patient's teeth.

This embodiment further contemplates that the keys also include an RCT (root canal therapy) key; a PFM (Porcelain Fused to Metal crown) key; an FGC (Full gold crown) key; an A.Prophy (Adult Prophy) key; a C.Prophy (Child Prophy) key; an SRP (Scaling and root planing) key; a Pontic (Middle fake tooth on a bridge) key; a Part Denture (partial Denture) key; and a Full Denture (Complete denture, no teeth on upper or lower arch).

This embodiment further contemplates that the keys also include an F (Facial or buccal) key; an L (Lingual or palatal, that is palate side or tongue side) key; a D (Distal, the back side of the tooth) key; an M (Mesial, the front side of the tooth) key; and an I/O (incisal or occlusal, the top side of the tooth or the chewing surface of the tooth —in the anterior teeth case that is called incisal) key.

This embodiment further contemplates a method for examining a patient's teeth during a dental exam comprising: providing a specialized dental keyboard having a plurality of keys, the plurality of keys comprising at least 32 keys wherein each key is consecutively numbered beginning with digit "1" and ending with the combination digits "32" indicating each one of the thirty-two teeth, and at least one additional key from the following group (an RCT (root canal therapy) key, a PFM (Porcelain Fused to Metal crown) key, an FGC (Full gold crown) key, an A.Prophy (Adult Prophy) key, a C.Prophy (Child Prophy) key, an SRP (Scaling and root planing) key, a Pontic (Middle fake tooth on a bridge) key, a Part Denture (partial Denture) key, or a Full Denture (Complete denture, no teeth on upper or lower arch key); providing a host computer with a dental examination software tool resident in memory; providing a software macro installed on the host computer, the software macro adapted to translate keystrokes of the specialized dental keyboard to data strings for inputting into the dental examination software tool; and the inputting of a sequence of keystrokes on the dental keyboard, the sequence of keystrokes representing a condition observed during the dental exam.

DRAWING

DESCRIPTION OF THE INVENTION

Possible embodiments will now be described with reference to the drawings and those skilled in the art will understand that alternative configurations and combinations of components may be substituted without subtracting from the invention. Also, in some figures certain components are omitted to more clearly illustrate the invention.

Figure 1:
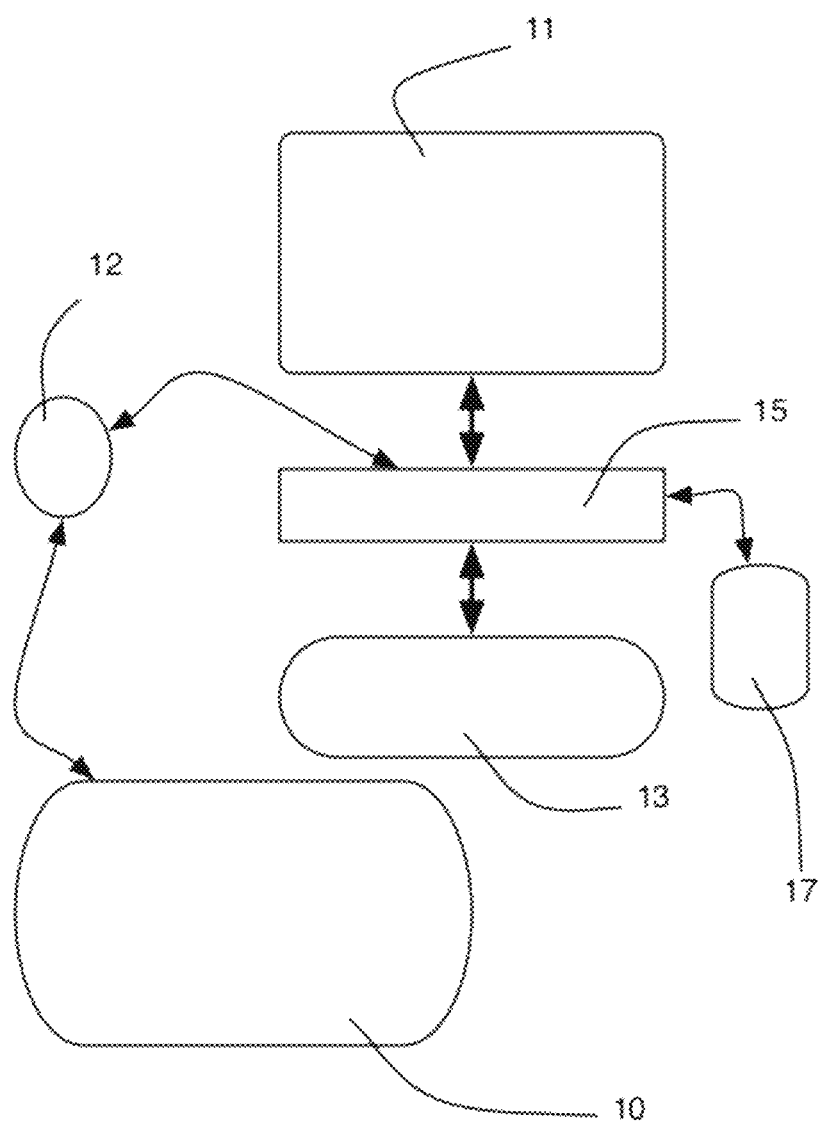
FIG. 1 is a system overview of one embodiment of the present invention.

FIG. 1 illustrates a system utilizing a specialized keyboard 10 according to a first preferred embodiment of the present invention. The specialized keyboard 10 or virtual keyboard 100 (FIG. 3) on a touchscreen communicates bi-directionally with a central processor on a computer 15. The communication between the specialized keyboard 10 or virtual keyboard 100 on a touchscreen and computer 15 may be facilitated by a communication means 12, such as a wireless sending receiving unit integrated (physically coupled to or physically integrated with) the specialized keyboard, such as a BLUETOOTH® enabled wireless transmitter/receiver. The traditional computer 15 includes a normal output device 11, such as a flat-panel display screen, CRT monitor, printer, and the like. Further, the computer 15 includes traditional input devices such as a keyboard 13 and mouse 17. An example of a suitable conventional computer system includes a desktop PC having an Intel Pentium-brand IV 2.4 GHz processing chip with 512 MB RAM-1 GB RAM, at least 2 GB available disk space (4), a CD-ROM Drive, an Ethernet 10/100/1000 network card, a standard CRT/LCD monitor with a minimum of 1024×768 screen resolution, 3D capable DirectX 9 compatible graphics card with 128 MB video memory (needed for 3D Modeling), a USB Chipset with two or more powered USB 2.0 ports, additional PCI Express, AGP, PCI or USB 2.0 expansion slots may be required, and a Windows-brand XP Professional operating system, for example.

FIG. 1 shows the specialized keyboard 10 or virtual keyboard 100 on a touchscreen as a separate physical entity from the communication means 12. It should be understood that the communication means includes, in one embodiment, separate, "black box" device that has wired connection to the computer 15 and keyboard 10 and includes software and hardware to convert signals from the keyboard 10 to standard code sequences for the computer and resident software to use conventionally as if keyed from the traditional associated keyboard 13.

In use, the present invention keyboard will be used instead of conventional input devices (for example, a conventional keyboard, touchscreen, mouse, pointer or a combination of these). Built-in software macros pre-loaded on the host computer will interpret keystrokes from the specialized keyboard of the present invention. The macros will then automatically feed the string of commands required by the specific software platform the dentist uses to manage patient care.

It should also be understood that the communication means 12, in an alternative embodiment, comprises a wired or wireless link between the specialized keyboard 10 or virtual keyboard 100 on a touchscreen and the processor on a conventional computer 15.

Other examples of conventional computer systems include Dell standard dental PC computers running either Windows XP or Vista. These systems commonly run dental software, such as Dentrix, Eaglesoft, Daisy, and Kodak dental software including support for specialty dental software such as Dolphin Dental Software.

Figure 2:
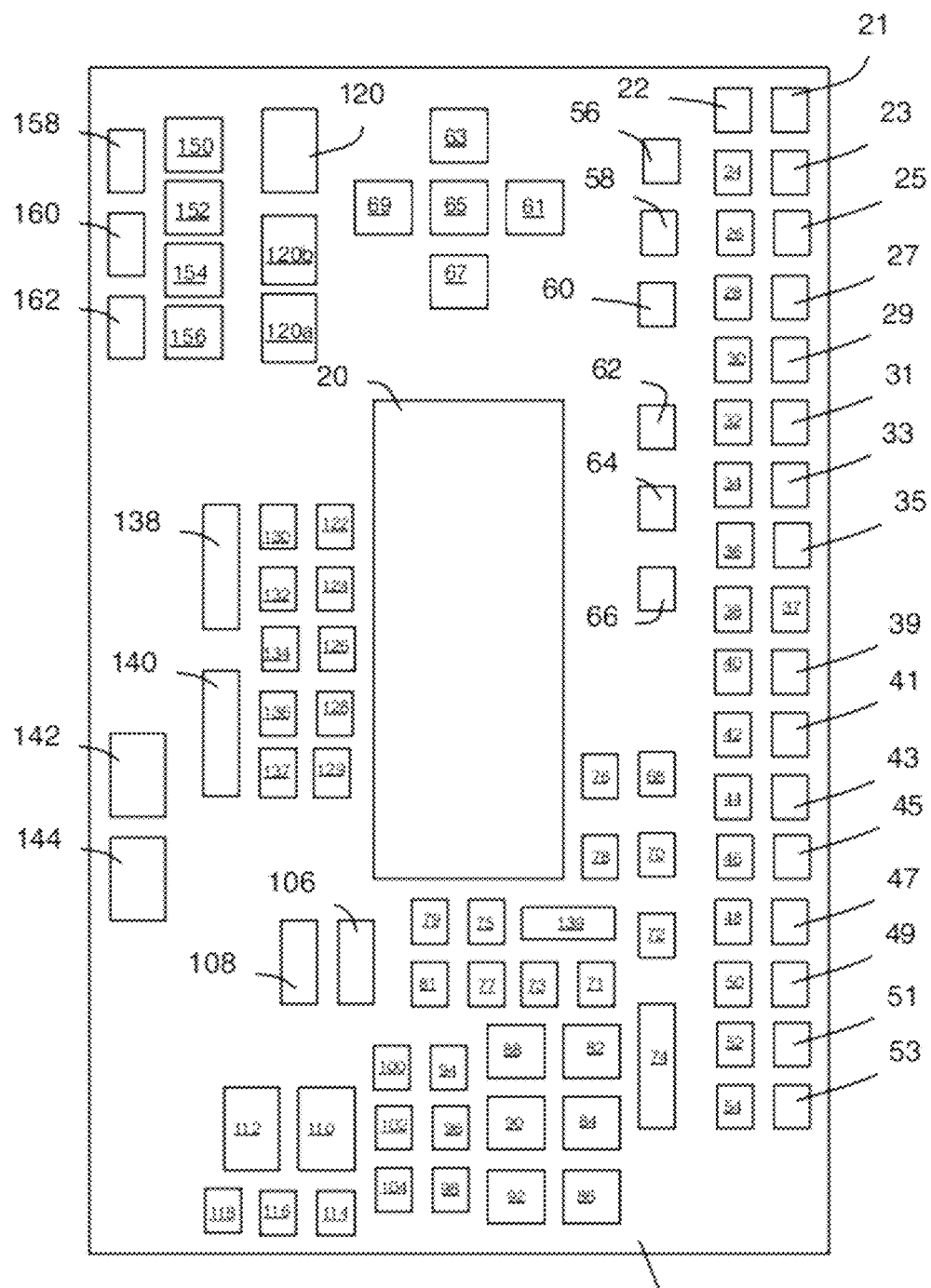
FIG. 2 is one possible keyboard layout or virtual key layout according to one embodiment of the present invention.

One contemplated layout for a specialized dental keyboard 10 according to the present invention, as FIG. 2 illustrates, includes an integrated display panel 20 and a plurality of specialized keys. One suitable display panel includes a device made by Samsung Electronics Co., Ltd. of Seoul, Korea and includes a design optimized for mobile applications consisting of a 7 inch diagonal viewing screen with a Si-TFT LCD Model that uses transparent plastic substrate that maintains constant thickness and will not break, even when bent. A full-color display delivers 640× 480×RBG (114 ppi) resolution with aperture ratio of 40%, brightness rating of 100 nit, and color saturation of 60% of NTSC, for example. The display panel 20 is used to flash the buttons pressed on an LCD screen for a couple of seconds to verify the data being sent to the computer, giving the operator a chance to verify they sent the correct data to the computer, or to cancel and reenter the data by pressing a cancel button.

The specialized keyboard 10 or virtual keyboard 100 on a touchscreen includes a first plurality of keys (reference numbers 21-54). This first plurality of keys consist of a first row of 17 keys and a second row of 17 keys, the first row being consecutively numbered from 1 to 16 (reference numbers 21, 23, 25, 27, 29, 31, 33, 35, 37, 39, 41, 43, 45, 47, 49, and 51, respectively), representing the correspondingly numbered teeth in a human mouth, plus one additional key to denote permanent teeth (reference number 53). The second row is also reverse consecutively numbered from 32 to 17 (reference number 22, 24, 26, 28, 30, 32, 34, 36, 38, 40, 42, 44, 46, 48, 50, and 52, respectively) representing the remaining teeth, plus one additional key to denote primary (baby) teeth (reference number 54). The sequence of keys in the first plurality of keys visually arranges as commonly displayed in graphical representations of teeth, which is quite familiar to dentists.

Additional individual keys are provided on the keyboard 10 including an "EX" key 56 for indicating the current condition of the tooth, a "DX" key 58 for indicating the diagnosis of the tooth, and a "TX" key 60 for indicating the prescribed treatment of the tooth.

Press the probing chart and the computer will automatically pull up the patient's periodontal chart.

On the right side of the device is the periodontal health of the tooth. It is represented with the most common buttons for millimeter readings of the periodontal pockets from 1-6 mm. The less common millimeter measurements are represented with smaller buttons 7-12 mm for each tooth. A bleeding point button can be pressed for the mesial, middle reading, and distal reading, for example, tooth #2 has a facial reading of 3-5-4 with bleeding points on both mesial and middle reading. The sequence of buttons that will be pressed are #2 on the upper left then b1, b2, on the probing chart 3-5-4 and then mobility I. This will give a very accurate reading of the existing periodontal condition of tooth #2.

Press the image capture button and the computer pulls up the intraoral camera.

The way pictures will be taken is that the assistant, for example, will press the #4 and the camera will become active and will point camera to #4, and the image will be stored in the patient's computer chart as tooth #4.

When the data is pulled for tooth #4, there will be an existing condition of what the patient's tooth looked like when they first joined the practice, along with an image of the tooth, the periodontal health of the tooth, what the proposed treatment was at the time and the treatment that was rendered on the tooth.

An assistant, doctor or hygienist can enter a full treatment plan on this keyboard 10 without having to use a mouse. Because using a mouse in the dental operatory is awkward, at best, and tends to really slow down the data entry, which causes the assistant to skip over pertinent data, this keyboard 10 improves the efficiency of the examination and also reduces data-entry errors.

The keyboard 10 includes specialized keys for typical examination procedures. Activating (or depressing) one of the specialized keys sends a data packet encoded to the computer 15, the data packet or string of information from the keyboard 10 is converted into conventional data as if entered via a mouse and graphical user interface or a conventional keyboard. The specialized key is essentially a "short cut" or "hot key" that enables one keystroke to replace an entire sequence of keystrokes or mouse clicks.

Common treatments and the corresponding specialized keys include: RCT (root canal therapy) key 134; PFM (Porcelain Fused to Metal crown) key 122; FGC (Full gold crown) key 124; A.Prophy (Adult Prophy) key 106; C.Prophy (Child Prophy) key 108; SRP (Scaling and root planing) key 139; Pontic (Middle fake tooth on a bridge) key 132; Part Denture (partial Denture) key 140 and Full Denture (Complete denture, no teeth on upper or lower arch) key 138, for example.

Additional specialized operations and corresponding keys on the specialized keyboard 10 or virtual keyboard 100 on a touchscreen are: F (Facial or buccal) key 61; L (Lingual or palatal, that is palate side or tongue side) key 69; D (Distal, the back side of the tooth) key 67; M (Mesial, the front side of the tooth) key 63; and I/o (incisal or occlusal, the top side of the tooth or the chewing surface of the tooth—in the anterior teeth case that is called incisal) key 65. These five keys are arranged in a cross pattern and are offset from other groupings of keys. The key layout is the standard layout of the shape of a tooth as depicted on the various dental software. This makes it effortless for the operator of the keyboard to enter the data on each tooth accurately and in a fast manner. Although the preferred embodiment, as illustrated in the appended drawing, describes a particular layout of keys thought to be advantageous in their layout for rapid data entry, other contemplated embodiments include additional keys, reduce the number of keys, or re-arrange the physical layout of keys, to provide alternate layouts as ergonomics or other criteria may dictate.

Other specialized operations and corresponding keys on the specialized keyboard 10 or virtual keyboard 100 on a touchscreen include: FMX (Full mouth series of X-rays) key 68; BW (bitewing x-ray) key 76; PA (Periapical x-ray) key 78; PANO (Panoramic X-ray) key 70; and Class V (filling a filling on the gum line of the tooth whether it is lingual or facial) key 120, for example.

The FMX, full mouth series of x-rays, corresponds to a full series of radiographs to be taken on a new patient's first visit. The BW are bitewing radiographs used to see in between teeth these radiographs are used to see in-between teeth.

The LCD display 20 displays the data entered and has a 2 sec. time lapse so that data can be reviewed prior to having it sent to the software. This way the person entering the data can intercept it and change it if he/she sees that they made a mistake in the data entry.

Using the keyboard of the present invention overcomes limitations in the existing art. Currently, a dentist must use a combination of a conventional keyboard and a mouse to select and input treatments, observed conditions, and current tooth condition (for example). The present invention, however, replaces the combination of screen, mouse, and conventional keyboard. Instead, the dentist rapidly uses the specialized keyboard of the present invention to capture a string of observations or treatment plans and observes the input on the small LCD screen prior to "entering" the sequence into the host computer.

Other contemplated physical structures of the specialized keyboard are contemplated including a laser keyboard such as an I-Tech Virtual Laser Keyboard available from Power Positioning Ltd of Grawn, Mich, or a flat panel or touch screen-type input device with reconfigurable keys based on a graphical user interface, or a membrane keyboard. Examples of membrane and touch screen input devices that could be adapted for use by the present invention include the devices manufactured by CSI Keyboards, Inc. of Peabody, Mass., USA, for example.

Figure 3:
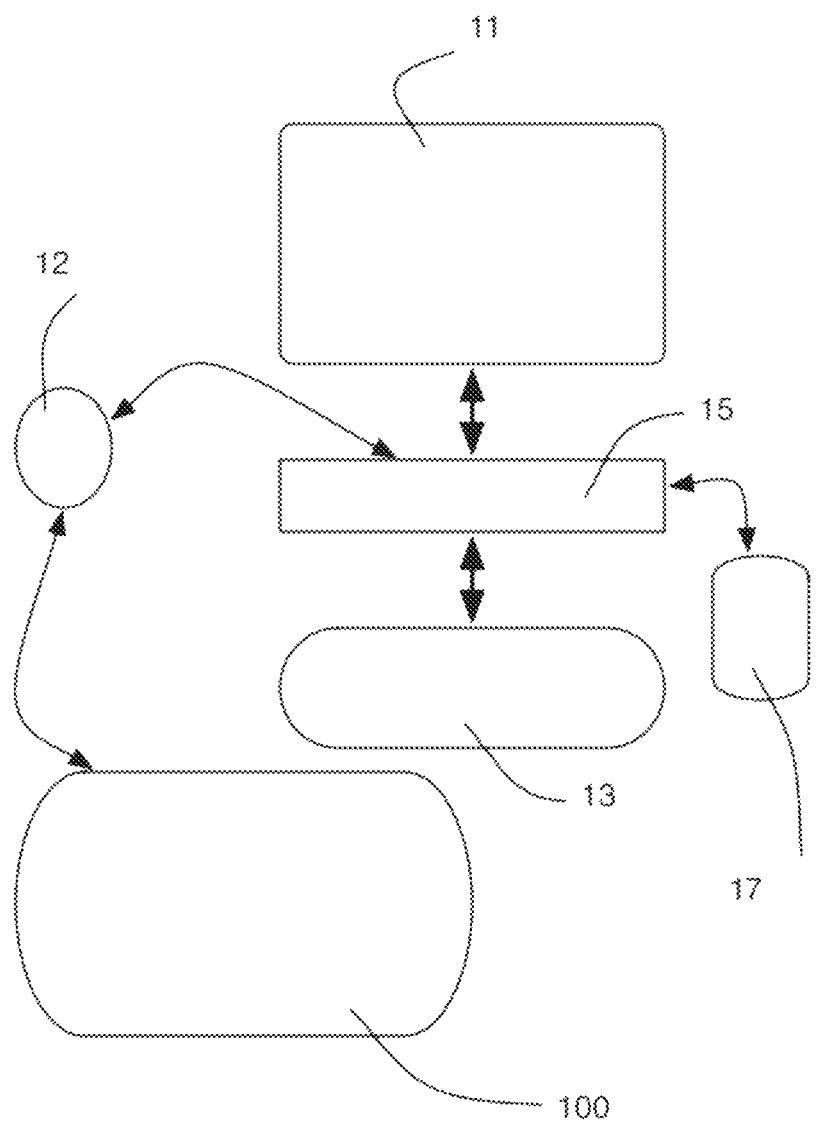
FIG. 3 is a system overview of a second embodiment of the present invention.
Figure 4:
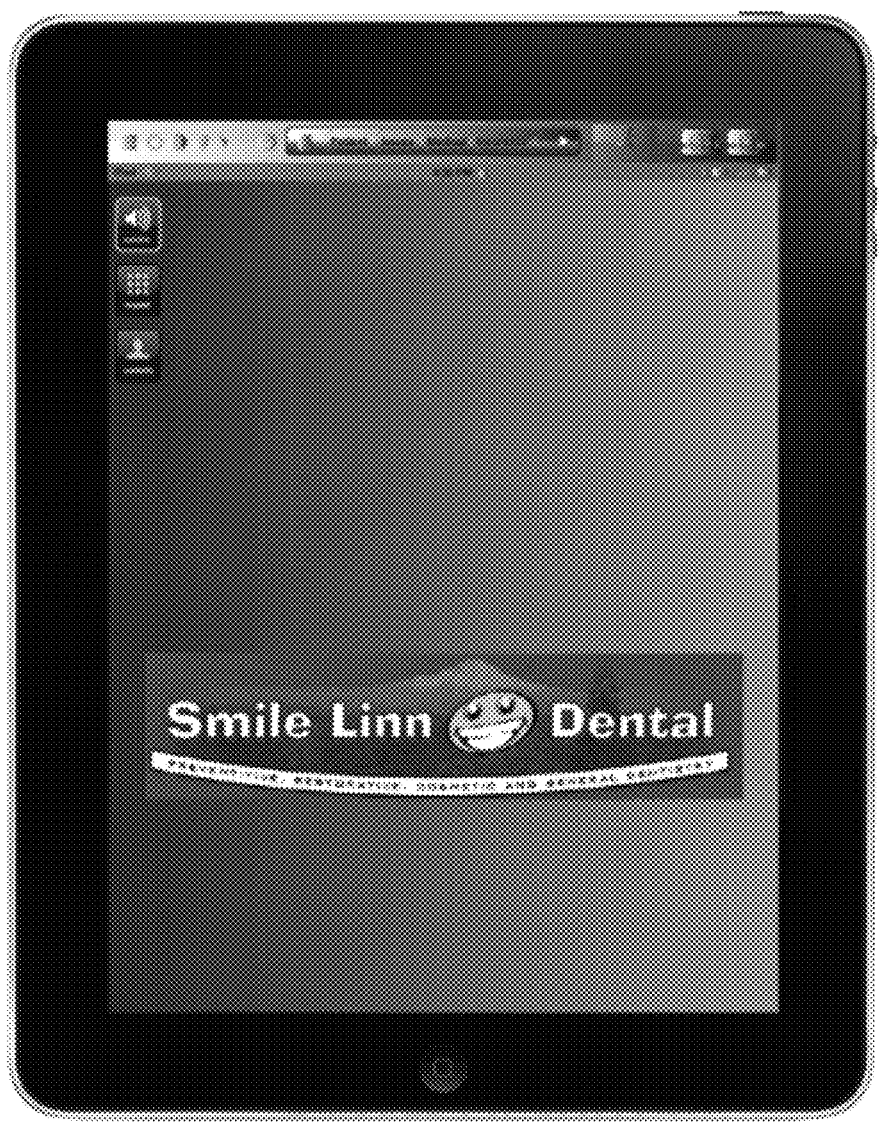
FIG. 4 is a virtual keyboard and graphical user interface combination of the present invention and shows an opening screen.
Figure 5:
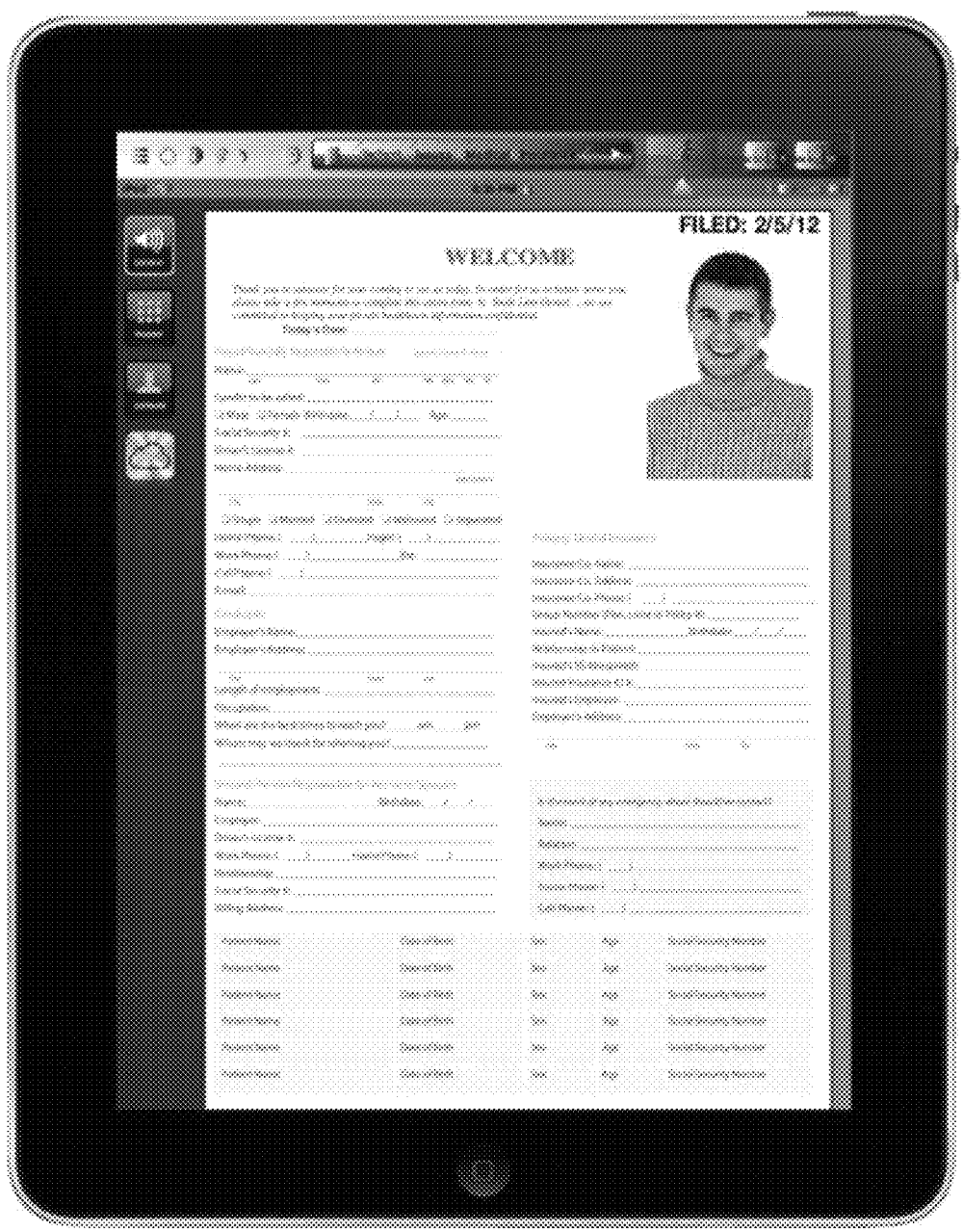
FIG. 5 is screen shot of a patient record on the touch screen tablet as contemplated by the second embodiment of the present invention.
Figure 6:
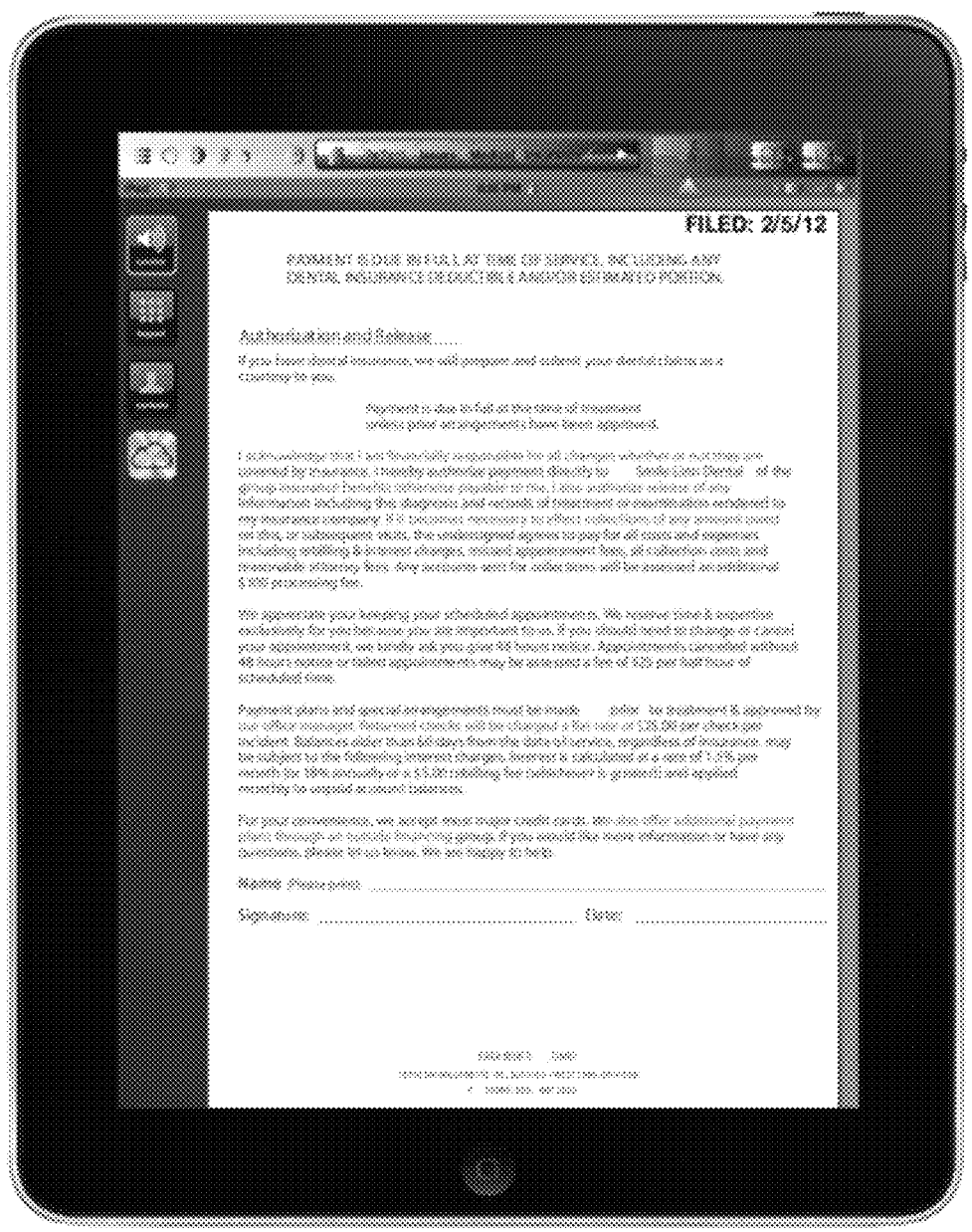
FIG. 6 is a screen shot of a patient disclosure form on the touch screen tablet as contemplated by the second embodiment of the present invention.
Figure 7:
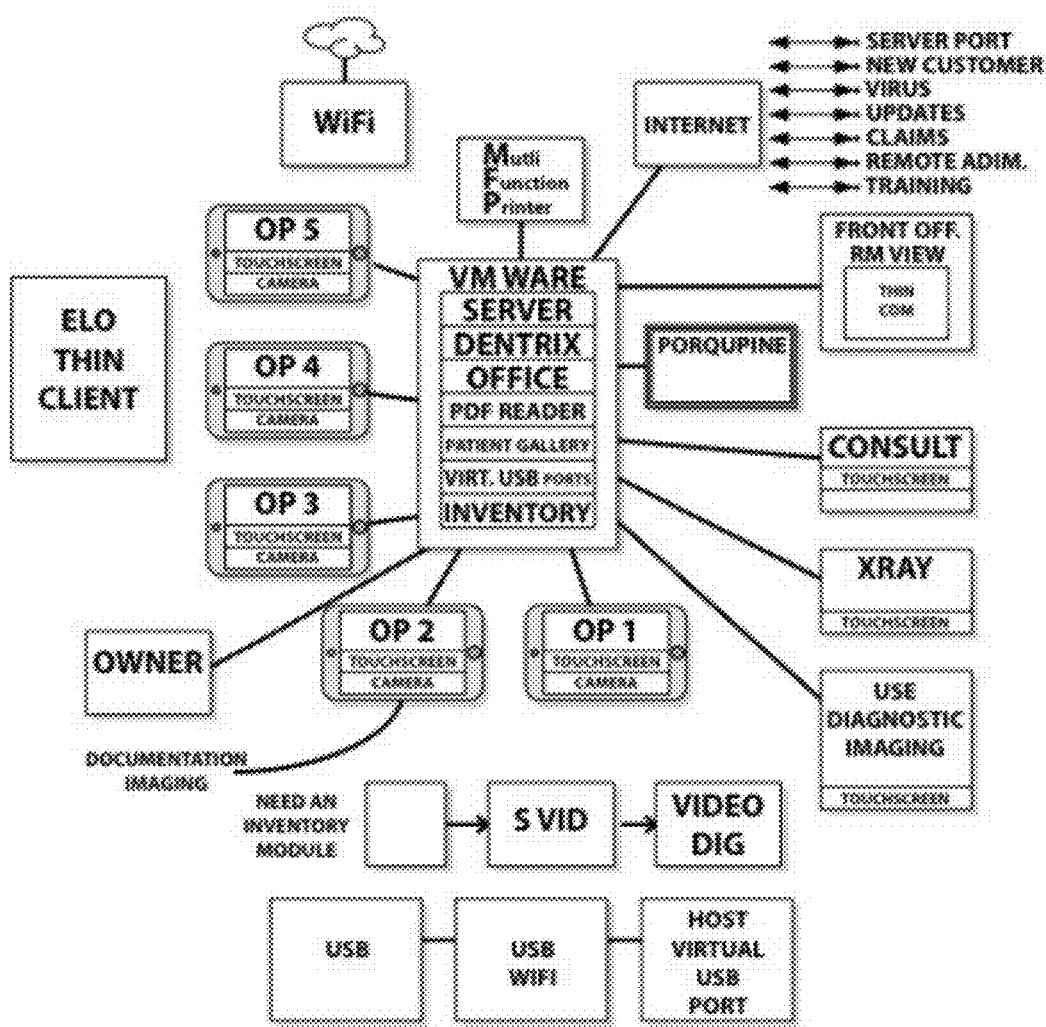
FIG. 7 is logic diagram of the virtual keyboard and software program of the second embodiment of the present invention.
Figure 8:
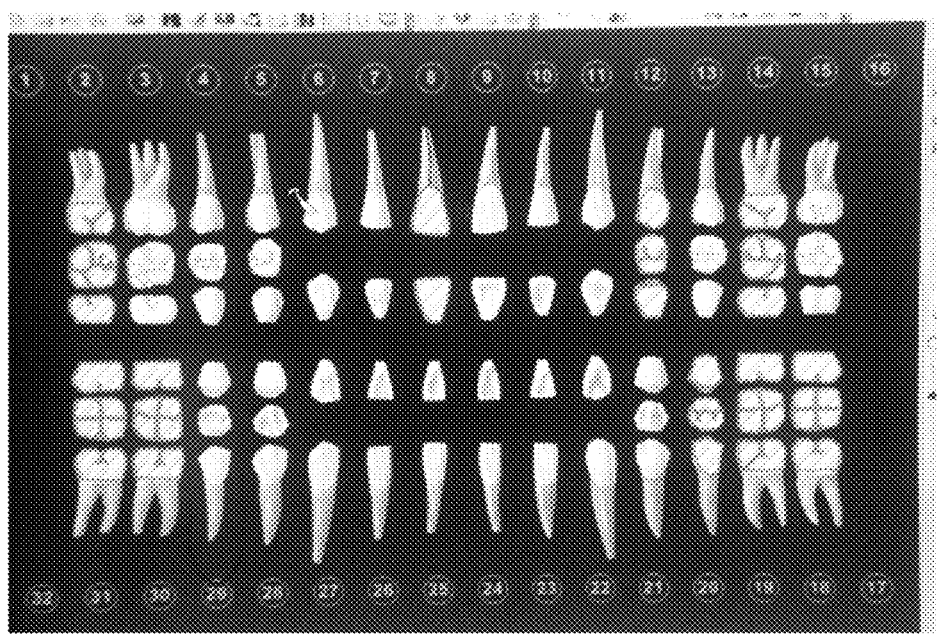
FIG. 8 is a possible virtual keyboard layout according to one embodiment of the present invention.
Figure 9:
FIG. 9 is another screen shot of a virtual keyboard and graphical user interface on the touch screen tablet as contemplated by the second embodiment of the present invention.
Figure 10:
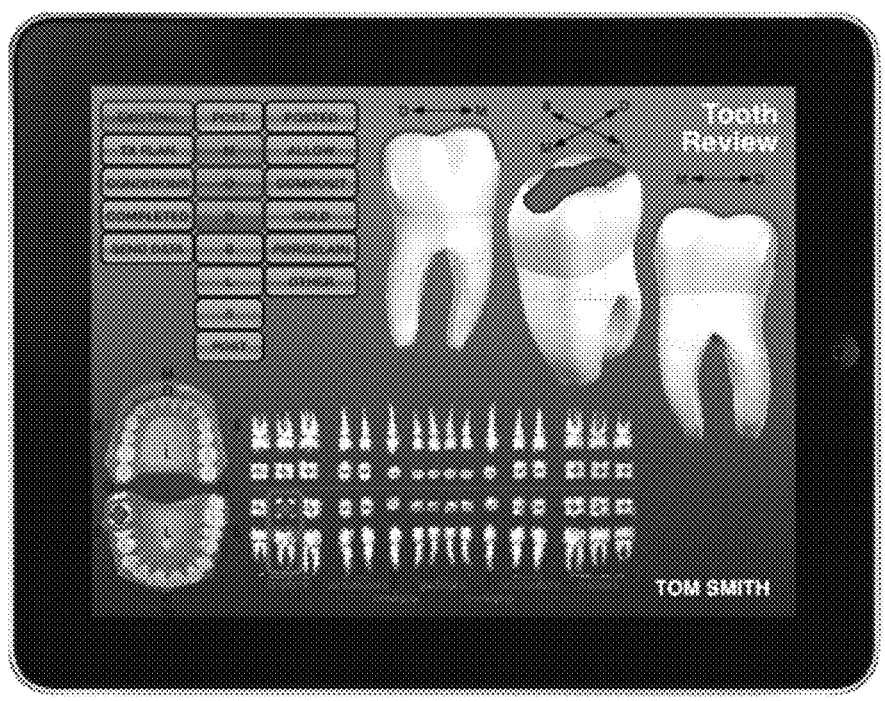
FIG. 10 is another screen shot of a virtual keyboard and graphical user interface on the touch screen tablet as contemplated by the second embodiment of the present invention.
Figure 11:
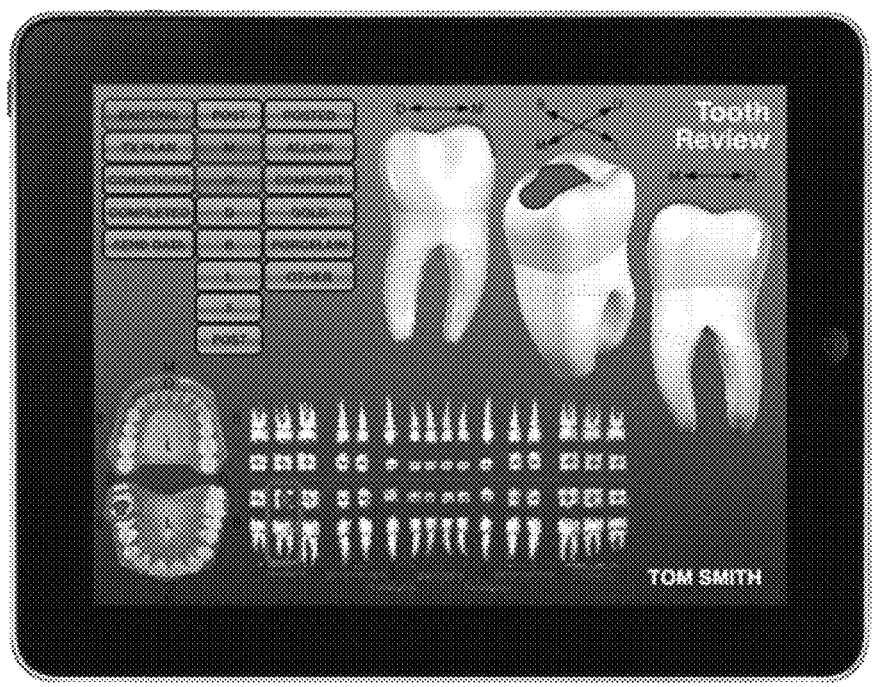
FIG. 11 is another screen shot of a virtual keyboard and graphical user interface on the touch screen tablet as contemplated by the second embodiment of the present invention.
Figure 12:
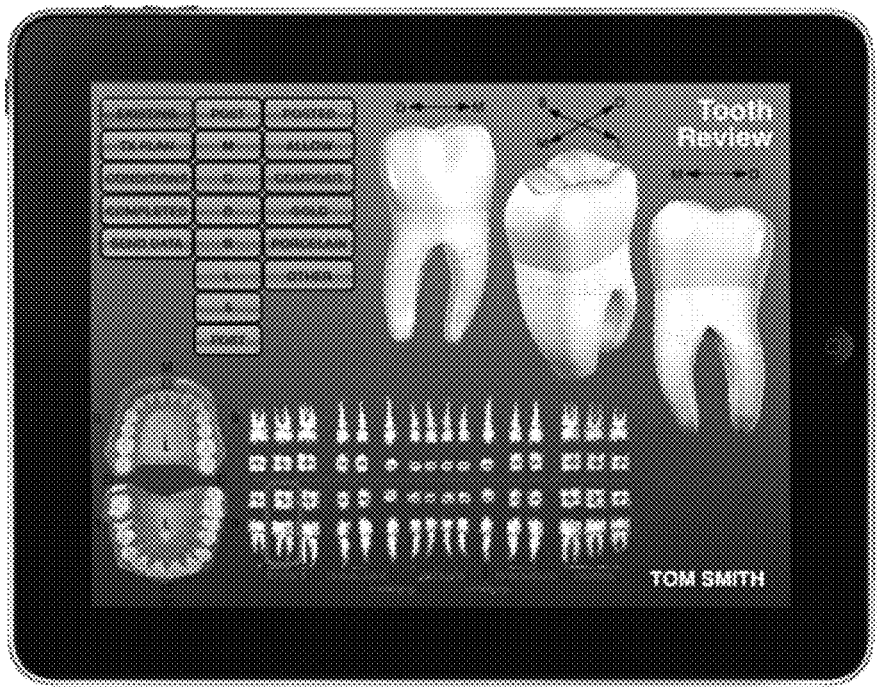
FIG. 12 is another screen shot of a virtual keyboard and graphical user interface on the touch screen tablet as contemplated by the second embodiment of the present invention.

As mentioned above, one embodiment of the contemplated present invention includes adapting a keyboard for use on a touchscreen device and is shown in FIGS. 3-1 2. The above buttons and keys can be directly translated to virtual buttons and keys rendered on a touchscreen device such as an iPad and the like by means well known and understood in the art. The reader is encouraged to contemplate the aforementioned physical, mechanical keys and buttons as virtual keys on the display of common touchscreen devices. Accordingly, a second preferred embodiment of the present invention contemplates use of the iPad or other similar tablet computer that includes a touchscreen input/output device.

One particularly well-suited embodiment of the present invention contemplates a software application ("app") adapted for use on a tablet computer including the Apple iPad (available from www.apple.com, for example) and other similar touch-screen interface tablet devices. In one preferred embodiment, the invention is ported for use on an iPad and details of this embodiment are described hereinafter, but should not be deemed limiting in scope because of the reference to a particular piece of hardware, but exemplary or representational of the spirit and scope of the present invention.

Digital x-ray images of a patient's teeth, jaw, and other related bone structure are common-place in today's dental office. Transferring the image from the digital x-ray recording device to a display associated with a personal computer is well-understood. Accordingly, transferring such an image to a touchscreen device is readily feasible by those of ordinary skill in this art. The present invention contemplates using this image on the touchscreen and overlaying a graphical representation of a single tooth so that details of observed conditions may be displayed for use by the dentist and patient. Further, recommended treatment, past treatment, and future conditions may also be graphically superimposed over the digital x-ray. Additionally, all the patient's teeth may be digitally x-rayed and a composite map of the patient's mouth using multiple x-ray images can be assembled so that all the teeth can be viewed simultaneously on the touch screen display. This also includes multiple views of each tooth and allows for graphical manipulation of each and every tooth in each and every view to demonstrate currently observed conditions of the teeth and/or to graphically display the proposed treatment options for any of the teeth.

Although the invention has been particularly shown and described with reference to certain embodiments, it will be understood by those skilled in the art that various changes in form and detail may be made without departing from the spirit and scope of the invention, and although claims are not required, I claim at least:

1. A specialized physical dental keyboard for recording conditions of teeth in a patient during a dental exam, the physical dental keyboard for use with a dental examination software tool resident on a host computer, the host computer having a central processor, at least one output screen or monitor device, and at least one input device, the physical dental keyboard being distinct from the screen or monitor device of the host computer and at least one input device, the 7 physical dental keyboard comprising:
   (a) a keyboard body having a plurality of mechanical input keys;
   (b) a first mechanical input key grouping having five mechanical input keys, each mechanical input key of the first mechanical input key grouping representing a tooth surface, comprising:
      (i) a central mechanical input key;
      (ii) a first side mechanical input key;
      (iii) a second side mechanical input key;
      (iv) a lower mechanical input key; and
      (v) an upper mechanical input key;
   (c) the central mechanical input key being centrally positioned between the first side mechanical input key, the second side mechanical input key, the lower mechanical input key, and the upper mechanical input key;
   (d) the central mechanical input key positioned between the first side mechanical input key and the second side mechanical input key without any intervening mechanical input keys therebetween, the central mechanical input key positioned between the upper mechanical input key and the lower mechanical input key without any intervening mechanical input keys therebetween;
   (e) the central mechanical input key, the first side mechanical input key, the second side mechanical input key, the lower mechanical input key, and the upper mechanical input key are arranged in a cross pattern;
   (f) the first mechanical input key grouping being offset from other mechanical input keys in that distances between adjacent mechanical input keys of the first grouping are smaller than the distances between the mechanical input keys of the first grouping and mechanical input keys not associated with the first grouping;
   (g) a second mechanical input key grouping, each mechanical input key of the second mechanical input key grouping representing a tooth, consisting of:
      (i) a first row and a second row of mechanical input keys, the first row and the second row each having 16 or 17 mechanical input keys;
   (h) the second mechanical input key grouping being offset from other mechanical input keys in that distances between adjacent mechanical input keys of the second grouping are smaller than the distances between the mechanical input keys of the second grouping and mechanical input keys not associated with the second grouping;
   (i) said physical dental keyboard having means for bi-directional communication with said dental examination software tool resident on said host computer;
   (j) wherein the first mechanical input key grouping facilitates both accuracy and speed of data entry of tooth surface information, and wherein the second mechanical input key grouping facilitates data entry of specific teeth.

2. The physical dental keyboard of claim 1 wherein said first row of at least 16 mechanical input keys is a first row of at least 16 mechanical input keys, and said second row of at least 16 mechanical input keys is a second row of at least 16 mechanical input keys.

3. The physical dental keyboard of claim 1 wherein said first row of at least 16 mechanical input keys is a first row of 17 mechanical input keys, and said second row of at least 16 mechanical input keys is a second row of 17 mechanical input keys.

4. The physical dental keyboard of claim 1 wherein said first row of at least 16 mechanical input keys is a first row of 17 mechanical input keys, or said second row of at least 16 mechanical input keys is a second row of 17 mechanical input keys.

5. The physical dental keyboard of claim 1 further comprising:
   (a) a third mechanical input key grouping, comprising:
      (i) a set of three mechanical input keys;
      (ii) wherein the third mechanical input key grouping is offset from other mechanical input keys in that distances between adjacent mechanical input keys of the second grouping are smaller than the distances between the mechanical input keys of the second grouping and mechanical input keys not associated with the second grouping.

6. The physical dental keyboard of claim 1 further comprising an integrated display panel to display a sequence of keystrokes.

7. The physical dental keyboard of claim 1 wherein the plurality of mechanical input keys further comprises an image capture mechanical input key.

8. The physical dental keyboard of claim 1 further comprising additional mechanical input keys related to dentistry.

9. The physical dental keyboard of claim 1 further comprising a second mechanical input key grouping, comprising:

(a) each mechanical input key of said first row of at least 16 mechanical input keys designating a specific tooth of the teeth of the upper arch of a mouth;
(b) each mechanical input key of said second row of at least 16 mechanical input keys designating a specific tooth of the teeth of the lower arch of a mouth;
(c) said first row of at least 16 mechanical input keys being positioned substantially adjacent said second row of at least 16 mechanical input keys to produce two rows of mechanical input keys without any intervening mechanical input keys; and
(e) the second mechanical input key grouping being offset from other mechanical input keys in that distances between adjacent mechanical input keys of the second grouping are smaller than the distances between the mechanical input keys of the second grouping and mechanical input keys not associated with the second grouping;
(f) wherein the second mechanical input key grouping facilitates data entry of specific teeth.

10. A specialized physical dental keyboard for recording conditions of teeth in a patient during a dental exam, the physical dental keyboard adapted to communicate bi-directionally with a dental examination software tool resident on a host computer, the host computer having a central processor, at least one output screen or monitor device, and at least one input device, the specialized physical dental keyboard being distinct from the screen or monitor device of the host computer, the physical dental keyboard comprising:
(a) a keyboard body having a plurality of mechanical input keys;
(b) a first mechanical input key grouping having five mechanical input keys, each mechanical input key of the first mechanical input key grouping representing a tooth surface, comprising:
  (i) a central mechanical input key;
  (ii) a first side mechanical input key;
  (iii) a second side mechanical input key;
  (iv) a lower mechanical input key; and
  (v) an upper mechanical input key;
(c) the central mechanical input key being centrally positioned between the first side mechanical input key, the second side mechanical input key, the lower mechanical input key, and the upper mechanical input key;
(d) the central mechanical input key positioned between the first side mechanical input key and the second side mechanical input key without any intervening mechanical input keys therebetween, the central mechanical input key positioned between the upper mechanical input key and the lower mechanical input key without any intervening mechanical input keys therebetween;
(e) the central mechanical input key, the first side mechanical input key, the second side mechanical input key, the lower mechanical input key, and the upper mechanical input key are arranged in a cross pattern;
(f) the first mechanical input key grouping being offset from other mechanical input keys in that distances between adjacent mechanical input keys of the first grouping are smaller than the distances between the mechanical input keys of the first grouping and mechanical input keys not associated with the first grouping;
(g) a second mechanical input key grouping, each mechanical input key of the second mechanical input key grouping representing a tooth, consisting of:
  (i) a first row and a second row of mechanical input keys, the first row and the second row each having 16 or 17 mechanical input keys;
(h) the second mechanical input key grouping being offset from other mechanical input keys in that distances between adjacent mechanical input keys of the second grouping are smaller than the distances between the mechanical input keys of the second grouping and mechanical input keys not associated with the second grouping;
(i) an integrated display panel to display a sequence of keystrokes.

11. The physical dental keyboard of claim 10 wherein said first row of at least 16 mechanical input key is a first row of 17 mechanical input keys, and said second row of at least 16 mechanical input keys is a second row of 17 mechanical input keys.

12. The physical dental keyboard of claim 10 wherein said first row of at least 16 mechanical input key is a first row of 17 mechanical input keys, or said second row of at least 16 mechanical input keys is a second row of 17 mechanical input keys.

13. The physical dental keyboard of claim 10 further comprising:
(a) a third mechanical input key grouping, comprising:
  (i) a set of three mechanical input keys;
  (ii) wherein the third mechanical input key grouping is offset from other mechanical input keys in that distances between adjacent mechanical input keys of the second grouping are smaller than the distances between the mechanical input keys of the second grouping and mechanical input keys not associated with the second grouping.

14. The physical dental keyboard of claim 10 wherein the plurality of mechanical input keys further comprises an image capture mechanical input key.

15. The physical dental keyboard of claim 10 further comprising additional mechanical input keys related to dentistry.

16. The physical dental keyboard of claim 10 further comprising a second mechanical input key grouping, comprising:
(a) each mechanical input key of said first row of at least 16 mechanical input keys designating a specific tooth of the teeth of the upper arch of a mouth;
(b) each mechanical input key of said second row of at least 16 mechanical input keys designating a specific tooth of the teeth of the lower arch of a mouth;
(c) said first row of at least 16 mechanical input keys being positioned substantially adjacent said second row of at least 16 mechanical input keys to produce two rows of mechanical input keys without any intervening mechanical input keys; and
(d) the second mechanical input key grouping being offset from other mechanical input keys in that distances between adjacent mechanical input keys of the second grouping are smaller than the distances between the mechanical input keys of the second grouping and mechanical input keys not associated with the second grouping.

17. A specialized physical dental keyboard for recording conditions of teeth in a patient during a dental exam, the physical dental keyboard adapted to communicate bi-directionally with a dental examination software tool resident on a host computer, the host computer having a central processor, at least one output screen or monitor device, and at least one input device, the physical dental keyboard comprising:

(a) a keyboard body having a plurality of mechanical input keys, five of the mechanical input keys being part of a first grouping of mechanical input keys, and at least thirty-two of the mechanical input keys being part of a second grouping keys;
(b) the first grouping of mechanical input keys arranged in a cross pattern, the first grouping of mechanical input keys offset from other mechanical input keys in that distances between adjacent mechanical input keys of the grouping are smaller than the distances between the mechanical input keys of the grouping and mechanical input keys not associated with the grouping, the first grouping of mechanical input keys including:
  (i) a central mechanical input key;
  (ii) a first side mechanical input key;
  (iii) a second side mechanical input key;
  (iv) a lower mechanical input key; and
  (v) an upper mechanical input key; and
(c) the second grouping of mechanical input keys, the second grouping consisting of:
  (i) a first row of and a second row of mechanical input keys, the first row and the second row each having 16 or 17 mechanical input keys, the first row being positioned substantially adjacent the second row of mechanical input keys to produce two rows of mechanical input keys without any intervening mechanical input keys; and
  (ii) the second mechanical input key grouping being offset from other mechanical input keys in that distances between adjacent mechanical input keys of the second grouping are smaller than the distances between the mechanical input keys of the second grouping and mechanical input keys not associated with the second grouping.

18. The physical dental keyboard of claim 17, wherein the first grouping of mechanical input keys and the second grouping keys are offset from each other in that distances between adjacent input keys of at least one of the groupings are smaller than the distance between the input key of the first grouping that is closest to the second grouping and the input key of the second grouping that is closest to the first grouping.

19. The physical dental keyboard of claim 17 further comprising an integrated display panel to display a sequence of keystrokes.

\* \* \* \* \*